United States Patent [19]

Miwa et al.

[11] Patent Number: 4,774,371

[45] Date of Patent: Sep. 27, 1988

[54] ADSORPTIVE SEPARATION PROCESS

[75] Inventors: Kishio Miwa; Yukiko Nagaoka, both of Kamakura; Takehisa Inoue, Tokyo; Kuniyuki Tada, Kamakura, all of Japan

[73] Assignee: Toray Industries, Inc., Tokyo, Japan

[21] Appl. No.: 848,839

[22] Filed: Apr. 3, 1986

Related U.S. Application Data

[63] Continuation of Ser. No. 604,071, Apr. 26, 1984.

[30] Foreign Application Priority Data

Apr. 28, 1983 [JP] Japan .................. 58-73855

[51] Int. Cl.$^4$ .......................................... C07C 17/38
[52] U.S. Cl. .................................. 570/211; 570/202
[58] Field of Search .............................. 570/211, 202

[56] References Cited

U.S. PATENT DOCUMENTS

| | | | |
|---|---|---|---|
| 2,882,244 | 4/1959 | Milton | 502/79 |
| 2,958,708 | 11/1960 | Fleck et al. | 570/211 |
| 3,013,985 | 12/1961 | Breck et al. | 502/78 |
| 3,135,809 | 6/1964 | Bosmajian | 570/202 |
| 3,560,579 | 2/1971 | Bacha et al. | 570/202 |
| 4,155,846 | 5/1979 | Novak et al. | 210/198.2 |
| 4,182,633 | 1/1980 | Ishikawa et al. | 210/198.2 |
| 4,254,062 | 3/1981 | Wambach et al. | 570/211 |
| 4,368,339 | 1/1983 | Toda et al. | 570/202 |

FOREIGN PATENT DOCUMENTS

| | | | |
|---|---|---|---|
| 46068 | 2/1982 | European Pat. Off. | 570/211 |
| 62261 | 10/1982 | European Pat. Off. | 570/202 |
| 72008 | 2/1983 | European Pat. Off. | 570/202 |
| 6626 | 12/1982 | Japan | 570/202 |

Primary Examiner—Werren B. Lone
Attorney, Agent, or Firm—Austin R. Miller

[57] ABSTRACT

A specific isomer of a trisubstituted benzene is continuously separated from a mixture containing at least two isomers of the trisubstituted benzene by adsorptive separation using a simulated moving bed, wherein a faujasite type zeolite adsorbent is used as the adsorpent and the specific isomer is separated as the extract component in the presence of a substituted benzene compound. The specific isomer to be separated is, for example, 2,6-dichlorotoluene, 3,5-dichlorotoluene and 2-chlorom-xylene. The substituted benzene compound is preferably a compound represented by the formula:

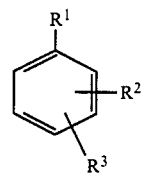

wherein
$R^1$ is H or $CH_3$, $R^2$ is H, $CH_3$ or Cl and $R^3$ is $CH_3$ or Cl, with the proviso that the case where $R^1$ is $CH_3$, $R^2$ is Cl and $R^3$ is Cl is excluded.

30 Claims, 2 Drawing Sheets

ADSORPTIVE SEPARATION PROCESS

This application is a continuation of application Ser. No. 604,071, filed Apr. 26, 1984.

BACKGROUND OF THE INVENTION

(1) Field of the Invention

The present invention relates to an adsorptive separation process for continuously separating a specific isomer of a trisubstituted benzene (such as 2,6-dichlorotoluene or other specific dichlorotoluene isomer) from a mixture containing at least two isomers of the trisubstituted benzene (such as a mixture of DCT isomers) by using a simulated moving bed.

(2) Description of the Prior Art

When a single isomer is prepared and recovered, the following problems inevitably arise in all conventional processes. In the first place, the formation ratio between an isomer formed as a by-product and an isomer to be recovered is not in agreement with the demanded ratio between the two isomers, and the by-product is a surplus and thus conventional processes are not preferred from the resource-saving viewpoint. In the second place, the difference of the boiling point between an isomer formed as by-product and an isomer to be recovered is so small that it is difficult to separate these isomers from each other by ordinary rectification, with the result that the separation process becomes complicated and a large quantity of energy is consumed for the process. The first problem may be solved by adoption of a process in which an isomer formed as a by-product is isomerized under isomerization reaction conditions and is converted to an isomer to be recovered. The second problem may be solved by adoption of a recovery process utilizing an adsorptive separation technique or crystallizing separation technique. However, solutions of both the problems are still insufficient.

For example, 2,6-dichlorotoluene (dichlorotoluene is hereinafter referred to as "DCT" for brevity) is an important intermediate for dyes, medicines and agricultural chemicals. However, since boiling points of DCT isomers are very close to one another, it is very difficult to separate 2,6-DCT from a DCT isomer mixture by rectification. Accordingly, 2,6-DCT is ordinarily prepared on an industrial scale, for example, by a process comprising dichlorination of p-toluene-sulfonic acid and subsequent desulfonation. However, a product having a high purity can hardly be obtained according to this process, and the process is not preferred from the economical viewpoint.

Furthermore, 3,5-DCT is expected as an intermediate for a novel agricultural chemical, but no industrial preparation process has been established because in the nuclear chlorination reaction of chlorotoluene the ortho- and para-orientations are strong and 3,5-DCT is hardly formed and because even if 3,5-DCT is formed by isomerization of other DCT isomers, the boiling point of 3,5-DCT is substantially equal to the other DCT isomers formed as by-products such as 2,4-DCT, 2,5-DCT and 2,6-DCT (having boiling points of about 200° C.) and it is substantially impossible to separate 3,5-DCT having a high purity by rectification.

U.S. Pat. No. 4,254,062 proposes a process for separating a specific DCT isomer from a DCT isomer mixture by using a zeolite of the faujasite type as an adsorbent. However, if it is intended to separate 2,6-DCT as the extract component, that is, as the highly adsorbable component, from a DCT isomer mixture, since the adsorbability of 2,3-DCT and/or 2,5-DCT to a zeolite of the faujasite is substantially equal to or higher than that of 2,6-DCT, it is substantially impossible to separate 2,6-DCT having a high purity.

Furthermore, the above mentioned U.S. patent does not refer to adsorptive separation of 3,5-DCT but discloses a separation technique to be applied to a system which does not substantially contain 3,5-DCT which is a nuclear chlorination product of toluene or chlorotoluene. Accordingly, it is not known whether the adsorptivity of a faujasite type zeolite adsorbent to 3,5-DCT is higher or lower than that of the adsorbent to other DCT isomers or whether or not it is possible to substantially separate 3,5-DCT having a high purity from a DCT isomer mixture by using this adsorbent.

SUMMARY OF THE INVENTION

It is a primary object of the present invention to provide a process for continuously separating at least one specific isomer of a trisubstituted benzene, e.g., a specific DCT isomer, from a mixture containing isomers of the trisubstituted benzene, e.g., a mixture of DCT isomers by using a simulated moving bed, wherein the intended isomer can be separated and recovered at a high efficiency and a high purity.

More specifically, in accordance with the fundamental aspect of the present invention, there is provided a process for continuously separating a specific isomer of a trisubstituted benzene from a mixture containing at least two isomers of the trisubstituted benzene by adsorptive separation using a simulated moving bed, wherein a faujasite type zeolite adsorbent is used as the adsorbent and the specific isomer is separated as the extract component in the presence of a substituted benzene compound.

Further, this invention provides a process for separating 2,6-dichlorotoluene from a mixture also containing at least its 2,3-isomer, by establishing a simulated moving adsorbent bed which includes an x-type zeolite as the adsorbent.

In accordance with the present invention, there are further provided (1) a process in which 2,6-DCT is separated as the extract component from a DCT isomer mixture containing 2,6-DCT, (2) a process in which 2,6-DCT and 2,4-DCT are separated as the extract component and raffinate component, respectively, from a DCT isomer mixture free of 3,5-DCT, (3) a process in which 2,6-DCT and 3,5-DCT are separated as the extract component and raffinate component, respectively, from a DCT isomer mixture containing 3,5-DCT and 2,6-DCT, (4) a process in which 3,5-DCT is separated as the extract component from a DCT isomer mixture containing 3,5-DCT, and (5) a process in which 2-chloro-m-xylene is separated as the extract component from a chloroxylene isomer mixture.

DETAILED DESCRIPTION OF PREFERRED EMBODIMENTS

In the continuous adsorptive separation technique according to the present invention, a simulated moving bed having a plurality of adsorption chambers filled with an adsorbent is used. This adsorptive separation technique comprises as the basic operations an adsorption operation, a concentration operation, a desorption operation and a desorbent recovery operation, which are continuously repeated. These basic operations are as follows.

(1) Adsorption Operation

A starting mixture is brought into contact with a bed of an adsorbent and a highly adsorbable component is selectively adsorbed. The remaining weakly adsorbable component is withdrawn from the adsorbent bed together with a desorbent in the form of a raffinate flow.

(2) Concentration Operation

The adsorbent having the strongly adsorbable component selectively adsorbed therein is brought into contact with a part of an extract described hereinafter to expel the weakly adsorbable component left on the adsorbent and increase the purity of the strongly adsorbable component.

(3) Desorption Operation

The adsorbent bed containing the strongly adsorbable component having an increased purity is brought into contact with the desorbent and the highly adsorbable component having the increased purity is withdrawn from the adsorbent bed together with the desorbent in the form of an extract flow.

(4) Recovery Operation

The adsorbent bed containing the desorbent is brought into contact with a part of the raffinate flow and the desorbent is withdrawn from the adsorbent bed.

Typical examples of the simulated moving bed operation will be described hereinafter in the working examples with reference to the accompanying drawings.

The faujasite type zeolite used in the process of the present invention is a crystalline aluminosilicate represented by the following formula:

wherein

M stands for a cation and n indicates the valency of the cation M.

The faujasite type zeolite represented by the above formula is classified into a type X in which x in the above formula is in the range of 2.5±0.5 and a type Y in which x in the above formula is from 3 to 6. The value of y in the above formula differs according to the degree of hydration. The faujasite type zeolite may be subjected to an aluminum-removing treatment.

Of the above-mentioned faujasite zeolites, the type X zeolite is preferred for separating 2,6-DCT as the extract component from a DCT isomer mixture. It also is preferred that the cation M be at least one member selected from metals of the groups IA, IB and IIA of the Periodic Table, thallium and ammonium ion, and it is especially preferred that the cation be at least one member selected from sodium, silver and cesium. A most preferred cation comprises 50 to 100 mole % of sodium, 0 to 50 mole % of silver and 0 to 50 mole % of cesium.

In the process for separating 3,5-DCT as the extract component from a DCT isomer mixture, it is preferred that the cation M be at least one member including sodium ion, and a most preferred cation comprises at least sodium and barium ions.

In the process for separating 2-chloro-m-xylene as the extract component from a chloroxylene isomer mixture, it is preferred that the cation M be at least one member selected from sodium, potassium, barium, calcium and silver.

The ion exchange process for the exchange of the cation M is well-known to experts in the art of the preparation of crystalline aluminosilicates. Ordinarily, the ion exchange is accomplished by bringing a zeolite into contact with an aqueous solution containing a soluble salt of at least one cation to be introduced into the zeolite.

The most important feature of the present invention resides in that a specific isomer is separated as the extract component in the presence of a substituted benzene compound.

In the process for separating 2,6-DCT as the extract component from a DCT isomer mixture, it is preferred that a compound represented by the following general formula (I):

wherein $R^1$ stands for H or $CH_3$, $R^2$ stands for H, $CH_3$ or Cl, and $R^3$ stands for $CH_3$ or Cl, with the proviso that the case where $R^1$ is $CH_3$, $R^2$ is Cl and $R^3$ is Cl is excluded, be used as the substituted benzene compound. More specifically, it is preferred that the substituted benzene compound be at least one member selected from toluene, xylene, chlorotoluene and trimethylbenzene, and it is more preferred that the substituted benzene compound be at least one member selected from o-xylene, m-xylene, p-xylene, o-chlorotoluene and p-chlorotoluene

In the process for separating 3,5-DCT as the extract component from a DCT isomer mixture, it is preferred that at least one compound selected from 1,2,4-trimethylbenzene and 2-chloro-p-xylene be used as the substituted benzene compound.

In the process for separating 2-chloro-m-xylene as the extract component from a chloroxylene mixture, it is preferred that at least one compound selected from toluene and chlorobenzene be used as the substituted benzene compound.

The substituted benzene compound used in the present invention may be added to the DCT isomer mixture or to the desorbent used in the simulated moving bed operation. It is preferable that the substituted benzene compound be used as the desorbent per se. This is because, in a simulated moving bed system as mentioned hereinbefore, an adsorbed component on an adsorbent is substituted by a desorbent in the desorption operation, and thus, a starting isomer mixture is brought into contact the adsorbent having adsorbed thereon substantially only the desorbent. In other words, the adsorption operation in a simulated moving bed system is always carried out in the presence of a desorbent, and therefore, when the desorbent is the substituted benzene compound itself, the adsorptive separation of the present invention can be advantageously effected.

The concentration of the substituted benzene compound in the adsorptive separation, which is expressed by the following formula:

100 (% by weight)

is at least 5% by weight, preferably at least 15%. When the substituted benzene compound is used as the desorbent, it is preferred that the feed ratio between the starting mixture and the desorbent be adjusted so that local reduction of the concentration of the substituted benzene compound in the separation system below 15% by weight is prevented.

In connection with the adsorptive separation conditions, the temperature is in the range of from room temperature to 350° C., preferably 50° to 250° C., and the pressure is in the range of from atmospheric pressure to 50 kg/cm$^2$·G, preferably from atmospheric pressure to 40 kg/cm$^2$·G. The isomer to be separated may be in the gas phase or in the liquid phase. However, it is preferred that the operation temperature be lowered and the operation be carried out in the liquid phase so as to control occurrence of undesirable side reactions of the starting mixture, substituted benzene compound and desorbent.

As pointed out hereinbefore, according to the present invention, by using a faujasite type zeolite adsorbent and continuously carrying out the adsorptive separation in a simulated moving bed in the presence of a substituted benzene compound, a specific isomer of a trisubstituted benzene can be separated and recovered as the extract from a mixture containing isomers of the trisubstituted benzene. The present invention is advantageously applied to the following separating and recovering processes.

(1) A process in which 2,6-DCT is separated as the extract component from a DCT isomer mixture containing 2,6-DCT, more specifically from a DCT isomer mixture containing 2,6-DCT and 2,3-DCT and/or 2,5-DCT.

(2) A process in which 2,6-DCT and 2,4-DCT are separated as the extract component and raffinate component, respectively, from a DCT isomer mixture containing 2,6-DCT and 2,4-DCT but not containing 3,5-DCT.

(3) A process in which 2,6-DCT and 3,5-DCT are separated as the extract component and raffinate component, respectively, from a DCT isomer mixture containing at least 2,6-DCT and 3,5-DCT.

(4) A process in which 3,5-DCT is separated as the extract component from a DCT isomer mixture containing at least 3,5-DCT.

(5) A process in which 2-chloro-m-xylene is separated as the extract component from a chloroxylene isomer mixture containing at least 2-chloro-m-xylene.

When 2,6-DCT is separated from a DCT isomer mixture containing at least 2,6-DCT, especially an isomer mixture containing 2,6-DCT and at least one member selected from 2,4-DCT, 2,5-DCT and 3,4-DCT (which may further contain 2,3-DCT), this separating step (a) may be combined with the step (b1) of isomerizing the raffinate component formed at the step (a). The isomer mixture formed at the isomerization step (b1) may be recycled to the step (a) of separating 2,6-DCT.

Furthermore, when 2,6-DCT is separated as the extract component, this separating step (a) may be combined with the isomerizing step (b2) of isomerizing a dichlorotoluene represented by the following formula (II), other than the dichlorotoluene to be prepared, or a dichlorotoluene isomer mixture containing said dichlorotoluene to be isomerized, in the presence of a catalyst composed of an acid type crystalline aluminosilicate zeolite having an X-ray diffraction pattern having peaks at lattice spacings d of 11.2±0.2 Å, 10.1±0.2 Å, 3.86±0.08 Å, 3.72±0.08 Å and 3.66±0.08 Å to increase the content of the dichlorotoluene to be separated and recovered:

wherein
one of X, Y and Z stands for CH$_3$ and the remaining members stand for Cl.

The isomerizing step (b2) will now be described in detail.

When DCT is isomerized, mutual conversion is preferentially caused in 3,4-DCT, 2,4-DCT and 2,5-DCT represented by the formula (II) among six isomers, that is, 2,3-DCT, 2,4-DCT, 2,5-DCT, 2,6-DCT, 3,4-DCT and 3,5-DCT. In short, group-selective isomerization is caused to occur. By the term "group-selective isomerization" used herein is meant selective isomerization of a specific group of isomers represented by the formula (II) among six isomers of DCT.

Accordingly, as the isomerization of DCT, the following three cases are very effective; that is, the case where 3,4-DCT is converted to 2,4-DCT and 2,5-DCT, the case where 2,4-DCT is converted to 3,4-DCT and 2,5-DCT and the case where 2,5-DCT is converted to 2,4-DCT and 3,4-DCT. Accordingly, the process comprises the separating step (a) and the isomerizing step (b2) is very effective for obtaining 2,4-DCT, 2,5-DCT and 3,4-DCT in addition to 2,6-DCT.

In the case where the concentration of the DCT isomer of the formula (II) to be separated, in the DCT isomer mixture from which 2,6-DCT has been separated, is approximately equal to or higher than the equilibrium concentration in the isomerization reaction, the DCT isomerization step (b2) is advantageously combined with a DCT separation step (C) as follows.

Namely, the raffinate component flowing out from the step (a) of separating 2,6-DCT is supplied to the step (C) of separating the specific isomer of the formula (II). Then, the remaining DCT isomer mixture is supplied to the isomerization step (2) where the concentration of the specific isomer of the formula (II) is increased. Thereafter, the DCT isomer mixture is recycled to the step (C) of separating the specific isomer of the formula (II).

In the case where the concentration of the DCT isomer of the formula (II) to be separated, in the DCT isomer mixture from which 2,6-DCT has been separated, is substantially zero or lower than the equilibrium concentration in the isomerization reaction, the DCT isomerization step (b2) is advantageously combined with a DCT separation step (C) as follows.

Namely, the DCT isomer mixture flowing out from the step (a) of separating 2,6-DCT is supplied to the isomerization step (b2) where the concentration of the specific isomer of the formula (II) is increased. Then, the DCT isomer mixture is supplied to the step (C) of separating the specific isomer of the formula (II), and thereafter, the remaining DCT isomer mixture is recycled to the isomerization step (b2).

A zeolite having a specific crystal structure is used for the isomerization reaction. Namely, a crystalline aluminosilicate zeolite having an X-ray diffraction pattern having peaks at positions of lattice spacings d of $11.2 \pm 0.2$ Å, $10.1 \pm 0.2$ Å, $3.86 \pm 0.08$ Å, $3.72 \pm 0.08$ Å and $3.66 \pm 0.08$ Å is used, and a crystalline aluminosilicate having an X-ray diffraction pattern having, in addition to the above-mentioned peaks, other peaks at positions of lattice spacings d of $6.00 \pm 0.1$ Å, $5.71 \pm 0.1$ Å, $5.58 \pm 0.1$ Å, $4.37 \pm 0.08$ Å, $4.27 \pm 0.08$ Å, $3.75 \pm 0.08$ Å and $3.00 \pm 0.05$ Å is more preferably used. As the zeolite of this type, there can be mentioned, for example, zeolite ZSM-5, the composition and preparation process of which are described in the specification of U.S. Pat. No. 3,894,104 and the crystal structure of which is described in Nature, 271, Mar. 30, 437 (1978), zeolite zeta-3 disclosed in Japanese Unexamined Patent Publication No. 51-67,298 and a zeolite disclosed in Japanese Patent Application No. 56-189,719 (crystalline aluminosilicate zeolite prepared by reacting an aqueous reaction mixture comprising a silica source, an alumina source, an alkali source and a carboxyl group-containing organic compound). Zeolite ZSM-5 and the zeolite disclosed in Japanese Patent Application No. 56-189,719 are especially preferred. It is preferred that the $SiO_2/Al_2O_3$ molar ratio in the zeolite be at least 10, especially in the range of from 15 to 100.

In the above-mentioned isomerization process, isomerization takes place only in 2,4-DCT, 2,5-DCT and 3,4-DCT, and 2,3-DCT, 2,6-DCT and 3,5-DCT are neither isomerized nor formed. For example, when 3,4-DCT is isomerized by using an aluminum chloride catalyst, five DCT isomers, that is, 2,3-DCT, 2,4-DCT, 2,5-DCT, 2,6-DCT and 3,5-DCT, are formed. In contrast, in the isomerizing process using the above-mentioned zeolite, unexpectedly, only 2,4-DCT and 2,5-DCT are formed and the other three DCT isomers are not formed. Accordingly, the 2,4-DCT and 2,5-DCT contents in the isomerization product liquid are high.

In the isomerization reaction, the zeolite is used in the form of an acid type. As is well known, the acid type zeolite contains a proton or a polyvalent cation having a valency of at least 2, such as a rare earth ion, as the cation of the zeolite. This acid type cation can be obtained by ion-exchanging at least a part of a metal ion of a zeolite having a monovalent alkali metal ion such as sodium with a proton or polyvalent cation or by ion-exchanging at least a part of such a metal ion with an ammonium cation, capable of being converted to a proton by sintering, and calcining the ion-exchanged zeolite. Ion exchange of the zeolite with the above-mentioned cation can be accomplished according to a known ion-exchanging process. For example, the ion exchange can easily be effected by treating the zeolite with an aqueous solution containing an acid, an ammonium salt or a water-soluble salt of a polyvalent cation. In case of a zeolite having an organic nitrogen-containing cation, such as zeolite ZSM-5, an acid type zeolite can be obtained by calcining this zeolite. Furthermore, there may optionally be adopted a method in which the residual alkali metal ion such as sodium in the zeolite is converted to a proton or ammonium cation according to a known ion-exchanging process, or a polyvalent cation having a valency of at least 2 may be introduced into the zeolite.

At the isomerizing step, the zeolite is used in the form of a molded body. The molding method is not particularly critical. For example, there may be adopted known methods such as the rolling method, extrusion method and compression method. Of course, a binder such as alumina sol or clay may be added at the molding step. The above-mentioned ion exchange may be carried out either before or after molding of the zeolite. The molded body of the zeolite is activated by calcining at 300° to 700° C. to obtain a catalyst.

For example, when 2,4-DCT having the formula (II) is prepared, a DCT isomer mixture left after separation of 2,4-DCT from a DCT isomer mixture containing 2,4-DCT is isomerized to increase the content of 2,4-DCT. This isomerization reaction may be carried out according to various known isomerization procedures. Either the liquid phase reaction or the gaseous phase reaction is possible, but in order to control occurrence of an undesirable side reaction such as decomposition, it is preferred that the isomerization be carried out in the liquid phase. Any of a fixed bed, a moving bed and a fluidized bed can be employed, but in view of the easiness in the operation, the fixed bed flow reactor is preferred. The reaction pressure is not particularly critical, but in case of the liquid phase reaction, the reaction pressure is set so that the liquid state is maintained. The reaction temperature is ordinarily in the range of from about 200° to about 500°, and a reaction temperature of 250° to 400° C. is preferred. The weight hourly space velocity (WHSV) is 0.05 to 30 $hr^{-1}$, preferably 0.1 to 20 $hr^{-1}$. If hydrogen, an aromatic compound such as benzene, or a chlorinated aromatic compound such as chlorobenzene is made present at the isomerizing step, there can be attained effects of controlling occurrence of side reactions and prolonging the catalyst life. Benzene and chlorobenzene are more preferably made present.

The embodiment where the step (a) of adsorptively separating 2,6-DCT is combined with the step of preparing 2,4-DCT or 3,4-DCT by isomerization and recovery will now be described with reference to the accompanying drawings.

Figure 2:
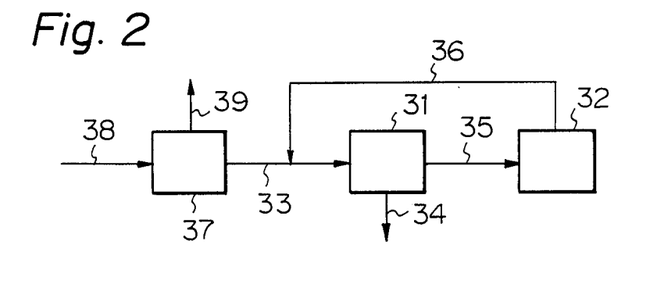
FIG. 2 is a flow sheet illustrating adsorptive separation of 2,6-DCT, and preparation of 2,4-DCT by isomerization and recovery thereof.

According to a typical process for obtaining a DCT isomer mixture containing 2,4-DCT and 2,6-DCT on an industrial scale, o-chlorotoluene which is obtained by nuclear chlorination of toluene is further subjected to nuclear chlorination, and the obtained isomer mixture contains 2,3-DCT, 2,4-DCT, 2,5-DCT and 2,6-DCT. Referring to FIG. 2 wherein the adsorptive separation of 2,6-DCT combined with the preparation of 2,4-DCT by isomerization is illustrated, the nuclear chlorination product 38 of o-chlorotoluene is supplied to a step 37 of the adsorptive separation of 2,6-DCT where 2,6-DCT 39 is separated and recovered. The remaining DCT isomer mixture 33 is supplied to a step 31 of separating 2,4-DCT where 2,4-DCT is adsorptively separated. Then, the remaining DCT isomer mixture 35 is supplied to an isomerization step 32 where the DCT isomer mixture is isomerized whereby the content of 2,4-DCT is increased. Then, the isomerized DCT isomer 36 mixture is recycled to the step 31 of adsorptive separation of 2,4-DCT.

At the isomerization step 32, 2,3-DCT is hardly isomerized. Accordingly, in order to prevent accumulation of 2,3-DCT in the circulation line of 35, 36, it is necessary to take out from the system a part of the DCT isomer mixture 35 left after the step 31 of adsorptive separation of 2,4-DCT. Alternately, 2,3-DCT contained in the DC isomer mixture 38 is preliminarily separated by rectification.

In the case where the DCT isomer mixture is a dichlorination product of toluene, the dichlorination product 38 in FIG. 2 further contains 3,4-DCT. Also in this case, it is possible to simultaneously prepare 2,6-DCT and 2,4-DCT as in the embodiment shown in FIG. 2.

Figure 3:
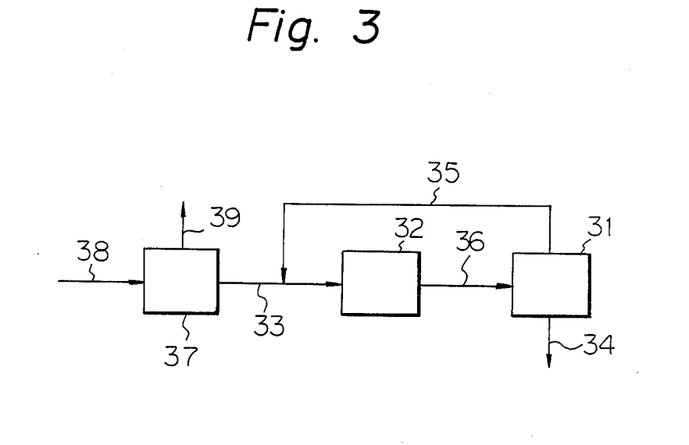
FIG. 3 is a flow sheet illustrating adsorptive separation of 2,6-DCT, and preparation of 3,4-DCT by isomerization and recovery thereof.

The embodiment where the step of adsorptive separation of 2,6-DCT is combined with the step of preparing 3,4-DCT by isomerization is exemplified in FIG. 3. Referring to FIG. 3, the above-mentioned DCT isomer mixture containing 2,3-DCT, 2,4-DCT, 2,5-DCT and 2,6-DCT which is a reaction product prepared by nuclear chlorination of o-chlorotoluene, is subjected to rectification whereby 2,3-DCT is separated from the DCT isomer mixture. The remaining DCT isomer mixture 38 is supplied to a step 37 of a adsorptive separation of 2,6-DCT where 2,6-DCT 39 is separated and recovered. Then, the remaining DCT isomer mixture 33, which is free from 3,4-DCT, is supplied to an isomerization step 32 where a part of the DCT isomer mixture 33 is isomerized to 3,4-DCT. The 3,4-DCT-containing isomer mixture 36 is supplied to a rectification step 31 where 3,4-DCT is separated from the DCT isomer mixture. Then, the remaining DCT isomer mixture 35 is recycled to the isomerization step 32.

Experiments of the adsorption characteristics where isomers were separated from dichlorotoluene isomer mixtures in the presence of a zeolite adsorbent and a substituted benzene compound will now be described.

In the Examples, the adsorption characteristic of the adsorbent is expressed by the adsorption selectivity $\alpha$ represented by the equation given below.

If it is noted that 2,6-DCT is separated as the extract component, the adsorption selectivity $\alpha_{2,6\text{-}DCT/X}$ is represented by the following equation:

$$\alpha_{2,6\text{-}DCT/X} = \frac{\left(\frac{\text{weight proportion of } 2,6\text{-}DCT}{\text{weight proportion of component } X}\right)_S}{\left(\frac{\text{weight proportion of } 2,6\text{-}DCT}{\text{weight proportion of component } X}\right)_L}$$

wherein
X stands for one of DCT isomers other than 2,6-DCT, S stands for the adsorption phase and L stands for the liquid phase equilibriated with the adsorption phase.

If all of the $\alpha$ values to DCT isomers other than 2,6-DCT, represented by the above equation, are larger than 1, 2,6-DCT can be separated as the extract component, that is, the highly adsorbable component. The substance to which the $\alpha$ value is close to 1 can hardly be separated from 2,6-DCT. The substance to which the $\alpha$ value is smaller than 1 flows into the extract component together with 2,6-DCT and 2,6-DCT having a high purity cannot be obtained.

If it is noted that 3,5-DCT (or 2,4-DCT) is separated as the raffinate component, the adsorption selectivity $\alpha_{X/3,5\text{-}DCT}$ (or 2,4-DCT) is expressed by the following equation:

$$\alpha_{X/3,5\text{-}DCT\,(or\,2,4\text{-}DCT)} = \frac{\left(\frac{\text{weight proportion of component } X}{\text{weight proportion of } 3,5\text{-}DCT \text{ or } 2,4\text{-}DCT}\right)_S}{\left(\frac{\text{weight proportion of component } X}{\text{weight proportion of } 3,5\text{-}DCT \text{ or } 2,4\text{-}DCT}\right)_L}$$

wherein
X stands for one of DCT isomers other than 3,5-DCT or 2,4-DCT, S stands for the absorption phase and L stands for the liquid
phase equilibriated with the adsorptionphase.

If all of the $\alpha$ values to DCT isomers other than 3,5-DCT or 2,4-DCT, represented by the above equation, are larger than 1, 3,5-DCT or 2,4-DCT can be separated as the raffinate component, that is, the weakly adsorbable component.

EXAMPLE 1

A powder of a zeolite of the Na-X type (SiO$_2$/Al$_2$O$_3$ molar ratio=2.5) was mixed with alumina sol as a binder in an amount of 15% by weight as Al$_2$O$_3$, and the mixture was kneaded and formed into granules having a size of 24 mesh to 32 mesh by extrusion molding. The granules were dried at 100° C. and calcined at 500° C. for 1 hour to obtain an adsorbent of the Na-X type.

The adsorbent was subjected to the ion exchange treatment with an aqueous solution of a nitrate at a solid/liquid ratio of 5 at a temperature of about 90° C. After the ion exchange treatment, the adsorbent was dried and calcined under the same conditions as described above with respect to the Na-X type.

In order to determine the adsorption selectivity of the adsorbent among DCT isomers, 2 g of the adsorbent and 3 g of a DCT isomer mixture were charged in an autoclave having an inner capacity of 5 ml, and the mixture was allowed to stand still at 130° C. for 1 hour in the presence of a substituted benzene compound shown in Table 1 below while the mixture was stirred now and then. The weight ratio of 2,3-DCT/2,4-DCT/2,5-DCT/2,6-DCT in the charged DCT isomer mixture was 12/18/37/33.

Furthermore, n-nonane was simultaneously charged as the reference substance for the gas-chromatography analysis in an amount of 20% by weight based on the DCT isomer mixture. Under the above adsorption conditions, n-nonane was substantially inert to the adsorptivity of the zeolite.

After contact with the adsorbent, the composition of the liquid phase mixture was analyzed by gas chromatography shown in Table 1.

In Table 1, the adsorbent for which a single cation component is indicated is an adsorbent in which said single cation occupies at least 90 equivalent % of the cations contained in the adsorbent. For example, the adsorbent 0.2Ag-Na-X indicates an adsorbent formed by subjecting the adsorbent of the Na-X type to the ion exchange treatment with an aqueous solution of silver nitrate containing Ag in an amount corresponding to 20 equivalent % of the Na cation.

In Table 1, the concentration of the substituted benzene compound is one calculated according to the following equation:

Concentration (% by weight) =

$$\frac{\text{substituted benzene compound}}{\text{DCT isomers + substituted benzene compound}} \times 100$$

TABLE 1

| Substituted Benzene Compound | Concentration (% by weight) of Substituted Benzene Compound | Adsorbent | $\alpha_{2,6-/2,5-}$ | $\alpha_{2,6-/2,4-}$ | $\alpha_{2,6-/2,3-}$ |
|---|---|---|---|---|---|
| Toluene | 90 | Na—X | 6.08 | 15.7 | 2.22 |
| | 50 | 0.2 Ag—Na—X | 4.77 | 8.70 | 2.53 |
| | 90 | 0.2 Ag—Na—X | 6.86 | 18.9 | 3.85 |
| o-Xylen | 90 | Na—X | 2.91 | 8.04 | 2.31 |
| | 50 | 0.2 Ag—Na—X | 3.74 | 6.22 | 2.17 |
| | 90 | 0.2 Ag—Na—X | 3.90 | 8.01 | 5.02 |
| | 50 | 0.2 Ag—Na—Y | 1.43 | 2.23 | 1.43 |
| | 50 | 0.2 Cs—Na—X | 2.38 | 5.05 | 1.90 |
| m-Xylene | 90 | Na—X | 3.47 | 8.67 | 2.42 |
| | 50 | 0.2 Ag—Na—X | 3.59 | 6.33 | 1.87 |
| | 90 | 0.2 Ag—Na—X | 6.10 | 13.40 | 2.96 |
| | 90 | 0.2 Cs—Na—X | 2.20 | 3.10 | 2.02 |
| p-Xylene | 90 | 0.2 Ag—Na—X | 9.00 | 22.3 | 5.5 |
| Xylene Isomer Mixture | 50 | 0.05 Ag—Na—X | 2.76 | 5.15 | 1.55 |
| (p/m/o = 2/5/30) | 90 | 0.05 Ag—Na—X | 4.53 | 9.41 | 3.77 |
| o-Chlorotoluene | 50 | 0.2 Ag—Na—X | 2.86 | 4.59 | 1.59 |
| m-Chlorotoluene | 90 | 0.2 Ag—Na—X | 2.57 | 4.65 | 1.11 |
| p-Chlorotoluene | 90 | 0.2 Ag—Na—X | 6.17 | 32.2 | 5.71 |
| 1,2,3-Trimethylbenzene | 50 | 0.2 Ag—Na—X | 2.44 | 4.62 | 2.09 |
| 1,2,4-Trimethylbenzene | 50 | 0.2 Ag—Na—X | 2.57 | 4.86 | 1.88 |

From the results shown in Table 1, it is seen that in the presence of the substituted benzene compound used in the present invention, 2,6-DCT can be separated as the extract component.

Examples wherein 2,6-DCT is separated from a DCT isomer mixture by using a simulated moving bed will now be described.

EXAMPLE 1-(A)

Figure 1:
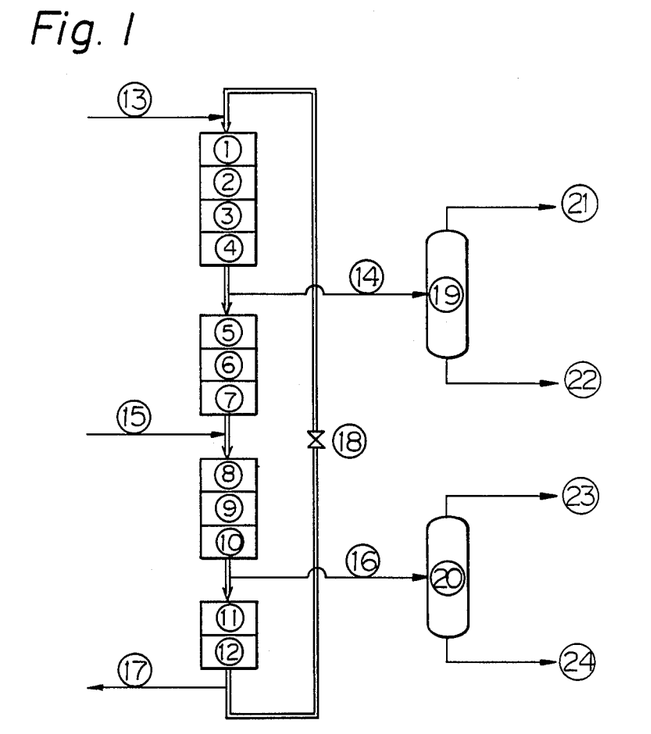
FIG. 1 is a flow sheet illustrating continuous adsorptive separation of 2,6-DCT using a simulated moving bed.

The simulated moving bed used will now be described with reference to FIG. 1. Twelve adsorption chambers 1 through 12 are connected in series, and reference numerals 13, 14, 15, 16 and 17 represent a desorbent feed line, an extract withdrawal line, a feed supply line, a raffinate withdrawal line and a desorbent recovery line, respectively. The desorption operation is carried out in the adsorpton chambers 1 through 4, the concentration operation is carried out in the adsorption chambers 5 through 7, the absorption operation is carried out in the absorption chambers 8 through 10, and the recovery operation is carried out in the absorption chambers 11 and 12. The liqued flows downward in the drawings. The line between the adsorption chambers 1 and 12 is closed by a valve 18. The extract and raffinate flows are separated into DCT components 22 and 24 and desorbent components 21 and 23 by rectifier columns 19 and 20.

At every predetermined time interval (hereinafter referred to as "changeover time"), the lines 13 through 17 and valve 18 are transferred counterclockwise by one adsorption chamber. If it is assumed that the above-mentioned lines and valve are kept stationary in FIG. 1, it may be considered that the adsorption chambers 1 through 12 are apparently transferred clockwise by one adsorption chamber in FIG. 1 by the above-mentioned operation. Thus, a simulated moving bed is constructed.

In the present example, each of the adsorption chambers having an inner capacity of about 13 ml was charged with 0.05Ag-Na-X having a size of 35 mesh to 60 mesh. A xylene isomer mixture (p/m/o ratio=2/5/3), one of the substituted benzene compounds used in the present invention, was supplied as the desorbent at a rate of 347 ml/hr from the line 13, and an extract flow was withdrawn at a rate of 125 ml/hr from the line 14. The above-mentioned DCT isomer mixture (containing 33% by weight of 2,6-DCT) was supplied at a rate of 11 ml/hr from the line 15 and a raffinate flow was withdrawn at a rate of 48 ml/hr from the line 16. The remaining liquid was withdrawn from the line 17. Each flow rate was one calculated as at room temperature.

The adsorption temperature was 150° C. and the changeover time was about 2.5 minutes.

The extract flow was distilled to separate the desorbent. The purity of 2,6-DCT in the remaining DCT component 22 was higher than 99.5% by weight. The content of 2,6-DCT in the DCT component 24 left after distillation of the raffinate flow was lower than 1% by weight.

In the above-mentioned operation, the desorbent, that is, the substituted benzene compound of the present invention, was present at a concentration higher than 50% by weight in the liquid in each adsorption chamber.

EXAMPLE 1-(B)

The above-mentioned procedures of Example 1-(A) were repeated in the same manner except that toluene was used as the desorbent and the adsorption temperature was changed to 130° C.

The purity of 2,6-DCT in the DCT component in the extract flow was higher than 99% by weight and the content of 2,6-DCT in the raffinate flow was lower than 3% by weight.

COMPARATIVE EXAMPLE 1

Adsorbents ion-exchanged with an aqueous nitrate solution were prepared according to the process described in Example 1. The adsorption selectivities among DCT isomers were measured by using these adsorbents under the same conditions as described in Example 1 except that the substituted benzene compound was not used. The obtained results are shown in Table 2.

TABLE 2

| Adsorbent | $\alpha_{2,6-/2,5-}$ | $\alpha_{2,6-/2,4-}$ | $\alpha_{2,6-/2,3-}$ |
|---|---|---|---|
| Na—X | 1.20 | 2.10 | 0.52 |
| K—X | 1.18 | 1.03 | 0.24 |
| Ca—X | 1.14 | 1.21 | 0.60 |
| 0.3Cr—Na—X | 0.96 | 1.40 | 0.44 |
| 0.3Ca—Na—X | 0.98 | 1.51 | 0.40 |
| 0.3Ni—Na—X | 0.93 | 1.45 | 0.39 |
| 0.3Sr—Na—X | 0.88 | 1.61 | 0.37 |
| 0.3Cs—Na—X | 1.04 | 2.22 | 0.74 |
| 0.3Mg—Na—X | 0.92 | 1.57 | 0.35 |
| 0.5Li—Na—X | 1.08 | 1.90 | 0.36 |
| 0.5Cu—Na—X | 0.98 | 1.01 | 0.56 |
| 0.1Ag—Na—X | 1.50 | 2.62 | 0.63 |
| 0.2Ag—Na—X | 1.95 | 2.83 | 0.82 |
| 0.4Ag—Na—X | 2.69 | 3.02 | 0.86 |
| 0.8Ba—K—X | 1.08 | 0.90 | 0.37 |
| 0.4Ag—K—X | 1.52 | 1.85 | 0.58 |
| 0.5Cu—Ca—X | 1.02 | 1.06 | 0.66 |
| 0.4Ag—Ca—X | 1.51 | 1.72 | 0.55 |

From the results shown in Table 2, it is seen that if the substituted benzene compound of the present invention is not used, all of the $\alpha_{2,6-/2,3-}$ values are smaller than 1.0. Namely, an adsorbent of a zeolite of the X type adsorbs 2,3-DCT more strongly than 2,6-DCT, and therefore, 2,6-DCT cannot be separated as the extract component. In adsorbents containing the cation other than Ag, the $\alpha_{2,6-/2,5}$ value is close to 1 and adsorptive separation of 2,6-DCT form 2,5-DCT is very difficult or substantially impossible. The adsorbents containing Ag as the cation makes it possible to separate 2,6-DCT from 2,5-DCT and separation of 2,6-DCT from 2,4-DCT can be performed more easily than by other adsorbents.

EXAMPLE 2

The adsorption selectivities among DCT isomers including 3,4-DCT were determined by using 0.2Ag-Na-X. The starting DCT isomer mixture was a mixture containing equal amounts of 2,6-DCT, 2,5-DCT, 2,4-DCT, 2,3-DCT and 3,4-DCT. Furthermore, the adsorption selectivities were measured in the presence of a substituted benzene compound. Other measurement conditions were the same as those described in Example 1. The obtained results are shown in Table 3.

From the results shown in Table 3, it is seen that in the absence of the substituted benzene compound used in the present invention, separation of 3,4-DCT from 2,6-DCT is substantially impossible, but if the substituted benzene compound of the present invention is used, 2,6-DCT can be separated as the extract component.

TABLE 3

| Adsorbent | Substituted Benzene Compound | $\alpha_{2,6-/3,4-}$ | $\alpha_{2,6-/2,5-}$ | $\alpha_{2,6-/2,4-}$ | $\alpha_{2,6-/2,3-}$ |
|---|---|---|---|---|---|
| 0.2Ag—Na—X | Not used | 1.06 | 1.55 | 2.40 | 0.73 |
| | o-Xylene (90 wt %) | 7.70 | 5.95 | 11.6 | 3.7 |

EXAMPLE 3

The adsorption selectivities among DCT isomers were measured by using the same adsorbents as used in Example 1 in the same manner as described in Example 1. In the charged DCT isomer mixture, the weight ratio of 2,3-DCT/2,4-DCT/2,5-DCT/2,6-DCT/3,4-DCT/3,5-DCT was 3.5/30.3/38.0/10.0/4.8/13.4. The obtained results are shown in Table 4.

TABLE 4

| Adsorbent | $\alpha_{2,3-/3,5-}$ | $\alpha_{2,4-/3,5-}$ | $\alpha_{2,5-/3,5-}$ | $\alpha_{2,6-/3,5-}$ | $\alpha_{3,4-/3,5-}$ |
|---|---|---|---|---|---|
| Na—X | 6.2 | 1.6 | 2.2 | 3.1 | 2.9 |
| K—X | 27.5 | 3.0 | 2.2 | 4.5 | 5.6 |
| Ca—X | 4.7 | 1.4 | 1.5 | 2.0 | 2.8 |
| 0.2Ag—Na—X | 9.6 | 2.1 | 2.6 | 6.0 | 5.3 |
| 0.3Cs—Na—X | 5.2 | 1.8 | 3.3 | 7.0 | 2.6 |
| 0.3Tl—Na—X | 4.8 | 1.8 | 2.8 | 5.4 | 2.5 |
| 0.3Mg—Na—X | 3.5 | 1.8 | 2.1 | 3.3 | 2.5 |

EXAMPLE 4

Adsorbents were prepared by using a powder of a zeolite of the Na-Y type ($SiO_2/Al_2O_3$ molar ratio=5.2) in the same manner as described in Example 1.

The adsorption selectivities α of the adsorbents of the Y type among DCT isomers were measured. The obtained results are shown in Table 5.

TABLE 5

| Adsorbent | $\alpha_{2,3-/3,5-}$ | $\alpha_{2,4-/3,5-}$ | $\alpha_{2,5-/3,5-}$ | $\alpha_{2,6-/3,5-}$ | $\alpha_{3,4-/3,5-}$ |
|---|---|---|---|---|---|
| 0.4Ag—Na—Y | 5.6 | 1.4 | 1.7 | 2.3 | 3.4 |
| 2.0Cu—Na—Y | 3.6 | 1.9 | 1.5 | 2.0 | 3.2 |

EXAMPLE 5

The adsorption selectivities among DCT isomers were measured by using the same adsorbents as used in Example 1 in the same manner as described in Example 1. In the charged DCT isomer mixture, the weight ratio of 2,3-DCT/2,4-DCT/2,5-DCT/2,6-DCT was 12/18/37/33. The obtained results are shown in Table 6.

TABLE 6

| Substituted Benzene Compound | Concentration (wt. %) of Substituted Benzene Compound | Adsorbent | $\alpha_{2,6-/2,4-}$ | $\alpha_{2,5-/2,4-}$ | $\alpha_{2,3-/2,4-}$ |
|---|---|---|---|---|---|
| Toluene | 90 | Na—X | 15.7 | 2.6 | 7.1 |
|  | 50 | 0.2 Ag—Na—X | 8.7 | 1.8 | 3.4 |
|  | 90 | 0.2 Ag—Na—X | 18.9 | 2.8 | 4.9 |
| o-Xylene | 90 | Na—X | 8.0 | 2.8 | 3.5 |
|  | 50 | 0.2 Ag—Na—X | 6.2 | 1.7 | 2.9 |
|  | 90 | 0.2 Ag—Na—X | 8.0 | 2.1 | 1.6 |
|  | 50 | 0.2 Ag—Na—Y | 2.2 | 1.6 | 1.6 |
|  | 50 | 0.2 Cs—Na—X | 5.1 | 2.1 | 2.7 |
| m-Xylene | 90 | Na—X | 8.7 | 2.5 | 3.6 |
|  | 50 | 0.2 Ag—Na—X | 6.3 | 1.8 | 3.4 |
|  | 90 | 0.2 Ag—Na—X | 13.4 | 2.2 | 4.5 |
|  | 90 | 0.2 Cs—Na—X | 3.1 | 1.4 | 1.5 |
| Xylene Isomer Mixture (p/m/o = 2/5/3) | 50 | 0.05 Ag—Na—X | 5.2 | 1.9 | 3.3 |
|  | 90 | 0.05 Ag—Na—X | 9.4 | 2.1 | 2.5 |

From the results shown in Table 6, it is seen that since all of the $\alpha_{X/2,4\text{-}DCT}$ values are larger than 1.0, 2,4-DCT can be separated as the raffinate component.

In all the combinations of adsorbents and desorbents shown in Table 6, the largest α value is the $\alpha_{2,6\text{-}/2,4\text{-}}$ value. This means that 2,6-DCT is most strongly adsorbed among the isomers in the DCT isomer mixture. Namely, 2,6-DCT can be separated as the extract component.

An example wherein 2,4-DCT is separated from a DCT isomer mixture by using a simulated moving bed will now be described.

The simulated moving bed used was the same as that described in Example 1-(A). The adsorption was carried out under the same conditions as in Example 1-(A) except the following changes. The desorbent was supplied at a rate of 331 ml/hr from the line 13, the extract flow was withdrawn at a rate of 127 ml/hr from the line 14, the same DCT mixture (containing 18% by weight of 2,4-DCT) as used in Example 1-(A) was supplied at a rate of 13 ml/hr from the line 15, and the raffinate flow was withdrawn at a rate of 11 ml/hr from the line 16. The purity of 2,4-DCT in the DCT component in the raffinate flow was higher than 99.5% by weight and the content of 2,4-DCT in the extract flow was lower than 1% by weight.

In the above-mentioned operation, the desorbent, that is, the substituted benzene compound of the present invention, was present at a concentration higher than 10% by weight in the liquid in each adsorption chamber.

EXAMPLE 6

The adsorption selectivities among DCT isomers including 3,4-DCT were measured by using 0.2Ag-Na-X. The charged DCT isomer mixture contained equal amounts of 2,6-DCT, 2,5-DCT, 2,4-DCT, 2,3-DCT and 3,4-DCT. Other measurement conditions were the same as described in Example 1. The obtained results are shown in Table 7.

TABLE 7

| Substituted Benzene Compound | Concentration (wt. %) of Substituted Benzene Compound | $\alpha_{2,6\text{-}/2,4\text{-}}$ | $\alpha_{2,5\text{-}/2,4\text{-}}$ | $\alpha_{2,3\text{-}/2,4\text{-}}$ | $\alpha_{3,4\text{-}/2,4\text{-}}$ |
|---|---|---|---|---|---|
| o-Xylene | 90 | 11.6 | 1.9 | 3.1 | 1.6 |

From the results shown in Table 7, it is seen that 2,4-DCT can be separated as the raffinate component and 2,6-DCT can be separated as the extract component.

EXAMPLE 7

According to the method described in the specification of Japanese Patent Application No. 56-189,719, an aqueous mixture comprising 66.0 g of white carbon (hydrous silicic acid), 17.47 g of sodium aluminate, 9.22 g of caustic soda, 12.5 g of tartaric acid and 344.2 g of water was maintained at 160° C. for 72 hours to effect crystallization and obtain a zeolite powder having an X-ray diffraction pattern shown in Table 8 and an $SiO_2/Al_2O_3$ molar ratio of 25.2.

TABLE 8

| X-Ray Diffraction Pattern | | | |
|---|---|---|---|
| d (Å) | $100I/I_{MAX}$ | d (Å) | $100I/I_{MAX}$ |
| 11.30 | 49 | 4.12 | 3 |
| 10.09 | 33 | 4.00 | 8 |
| 9.82 | 11 | 3.86 | 100 |
| 9.11 | 6 | 3.83 | 82 |
| 7.51 | 5 | 3.76 | 50 |
| 7.14 | 2 | 3.74 | 55 |
| 6.75 | 8 | 3.66 | 27 |
| 6.59 | 6 | 3.62 | 5 |
| 6.40 | 9 | 3.50 | 8 |
| 6.04 | 12 | 3.47 | 15 |
| 5.75 | 10 | 3.38 | 9 |
| 5.61 | 13 | 3.33 | 8 |
| 5.40 | 2 | 3.27 | 2 |
| 5.17 | 3 | 3.23 | 2 |
| 5.02 | 8 | 3.20 | 2 |
| 4.63 | 4 | 3.16 | 2 |
| 4.52 | 3 | 3.06 | 10 |
| 4.39 | 10 | 2.99 | 16 |
| 4.29 | 8 | | |

This zeolite powder was mixed with alumina sol in an amount of 15% by weight as $Al_2O_3$, the the mixture was kneaded and extrusion-molded into granules having a size of 14 mesh to 24 mesh. The granules were calcined in air at 500° C. for 2 hours. The obtained zeolite molded body was ion-exchanged 5 times with an aqueous solution containing 10% by weight of ammonium chloride at a solid-liquid ratio of 2.0 l/kg and a temperature of about 90° C. The molded body was sufficiently washed with water, dried at 120° C. for 15 hours and calcined at 600° C. in air for 2 hours to obtain a zeolite catalyst of the acid type.

Isomerization of 3,4-DCT was carried out by using this catalyst in the liquid phase in the presence of benzene in a fixed bed flow reactor under the following reaction conditions.

Composition of feed liquid: 3,4-DCT/benzene weight ratio=2/1
WHSV (based on DCT): 0.4 hr$^{-1}$
Reaction temperature: 310° C.
Reaction pressure: 30 kg/cm$^2$·G The DCT isomer mixture obtained by the reaction comprised 20.9% by weight of 2,5-DCT, 26.3% by weight of 2,4-DCT and 52.7% by weight of 3,4-DCT. None of 2,3-DCT, 2,6-DCT and 3,5-DCT were formed.

COMPARATIVE EXAMPLE 2

A three-neck flask having an inner capacity of 300 ml was charged with 0.5 mole of 3,4-DCT, 0.05 mole of AlCl$_3$ and 1 ml of water, and reaction was carried out with stirring at 150° to 160° C. for 1.5 hours. The DCT isomer mixture obtained by the reaction comprised 12.3% by weight of 2,5-DCT, 2.1% by weight of 2,6-DCT, 10.4% by weight of 3,5-DCT, 16.8% by weight of 2,4-DCT, 50.0% by weight of 3,4-DCT and 11.4% by weight of 2,3-DCT. Thus, it is seen that when an AlCl$_3$ catalyst is used, all the DCT isomers are formed. Although the isomerization ratio of starting 3,4-DCT was substantially equal to the isomerization ratio in Example 7, the contents of 2,4-DCT and 2,5-DCT in the liquid reaction mixture were lower than in Example 7.

EXAMPLE 8

By using the same zeolite catalyst of the acid type as used in Example 7, isomerization of 2,4-DCT was carried out in the presence of benzene in the liquid phase in a fixed bed flow reactor under the following conditions.

Composition of feed liquid: 2,4-DCT/benzene weight ratio=2/1
WHSV (based on DCT): 0.4 hr$^{-1}$
Reaction temperature: 310° C.
Reaction pressure: 30 kg/cm$^2$·G The DCT isomer mixture obtained by the reaction comprised 35.7% by weight of 2,5-DCT, 55.9% by weight of 2,4-DCT and 8.4% by weight of 3,4-DCT. None of 2,3-DCT, 2,6-DCT and 3,5-DCT were formed.

EXAMPLE 9

According to the process disclosed in Japanese Unexamined Patent Publication No. 50-54,598, an aqueous mixture comprising 135 g of sodium silicate, 14.4 g of Al$_2$(SO$_4$)$_3$·18H$_2$O, 15 g of n-propylamine, 11.2 g of H$_2$SO$_4$ and 400 g of water was maintained at 155° C. for 72 hours to effect crystallization and thereby obtain a powder of zeolite ZSM-5 having an X-ray diffraction pattern shown in Table 9 and an SiO$_2$/Al$_2$O$_3$ molar ratio of 26.4.

TABLE 9

X-Ray Diffraction Pattern

| d (Å) | 100I/I$_{MAX}$ | d (Å) | 100I/I$_{MAX}$ |
|---|---|---|---|
| 11.32 | 55 | 4.30 | 30 |
| 10.20 | 34 | 4.15 | 11 |
| 7.51 | 2 | 4.05 | 8 |
| 6.77 | 6 | 3.89 | 100 |
| 6.05 | 9 | 3.75 | 51 |
| 5.76 | 7 | 3.67 | 24 |
| 5.62 | 10 | 3.50 | 7 |
| 5.41 | 2 | 3.46 | 7 |
| 5.19 | 4 | 3.33 | 10 |
| 5.04 | 5 | 3.27 | 4 |
| 4.65 | 7 | 3.07 | 8 |
| 4.39 | 11 | 3.00 | 11 |

This powder of zeolite ZSM-5 was mixed with alumina sol in an amount of 15% by weight as Al$_2$O$_3$, and the mixture was kneaded and extrusion-molded into granules having a size of 14 mesh to 24 mesh. The granules were calcined in air at 500° C. for 2 hours. The molded body of zeolite ZSM-5 was ion-exchanged 5 times with an aqueous solution containing 10% by weight of ammonium chloride at a solid-liquid ratio of 2.0 l/kg and a temperature of about 90° C., and the molded body was sufficiently washed with water, dried at 120° C. for 15 hours and calcined in air at 600° C. for 2 hours to obtain an acid type ZSM-5 catalyst. By using the thus-obtained acid type ZSM-5 catalyst, isomerization of 2,4-DCT was carried out in the liquid phase in the presence of benzene in a fixed bed flow reactor under the following conditions.

Composition of feed liquid:
2,4-DCT/benzene weight ratio=2/1
WHSV (based on DCT): 0.4 hr$^{-1}$
Reaction temperature: 290° C.
Reaction pressure: 30 kg/cm$^2$·G The DCT isomer mixture obtained by the reaction comprised 13.8% by weight of 2,5-DCT, 82.2% by weight of 2,4-DCT and 4.0% by weight of 3,4-DCT, and none of 2,3-DCT, 2,6-DCT and 3,5-DCT were formed.

EXAMPLE 10

By using the same zeolite catalyst of the acid type as used in Referential Example 7, isomerization of 2,4-DCT was carried out in the liquid phase in the presence of chlorobenzene in a fixed bed flow reactor under the following conditions.

Composition of feed liquid:
2,4-DCT/chlorobenzene weight ratio=2/1
WHSV (based on DCT): 0.4 hr$^{-1}$
Reaction temperature: 290° C.
Reaction pressure: 30 kg/cm$^2$·G The DCT isomer mixture obtained by the reaction comprised 12.4% by weight of 2,5-DCT, 84.2% by weight of 2,4-DCT and 3.4% by weight of 3,4-DCT, and none of 2,3-DCT, 2,6-DCT and 3,5-DCT were formed.

COMPARATIVE EXAMPLE 3

A powder of synthetic mordenite of the sodium type was mixed with alumina sol in an amount of 15% by weight as Al$_2$O$_3$, and the mixture was kneaded and extrusion-molded into granules having a size of 14 mesh to 24 mesh. The granules were calcined in air at 500° C. for 2 hours. The mordenite molded body was ion-exchanged 5 times with an aqueous solution containing 10% by weight of ammonium chloride at a solid-liquid ratio of 2.0 l/kg and a temperature of about 90° C. The molded body was sufficiently washed with water, dried at 120° C. for 15 hours and calcined in air at 500° C. for 2 hours to obtain a mordenite catalyst of the acid type.

By using the thus-obtained catalyst, isomerization of 3,4-DCT and 2,4-DCT was carried out in the liquid phase in the presence of benzene in a fixed bed flow reactor under the following reaction conditions.

Composition of feed liquid:
DCT/benzene weight ratio=2/1
WHSV (based on DCT): 0.4 hr$^{-1}$
Reaction temperature: 300° C.
Reaction pressure: 30 kg/cm$^2$·G The DCT composition after the reaction was as shown in Table 10.

TABLE 10

Results of Isomerization of DCT

| DCT Composition (% by weight) in Formed Reaction Liquid | Feed DCT 3,4-DCT | Feed DCT 2,4-DCT |
|---|---|---|
| 2,5-DCT | 0.8 | 2.8 |
| 2,6-DCT | — | 0.1 |
| 3,5-DCT | — | 0.2 |
| 2,4-DCT | 9.9 | 95.7 |
| 3,4-DCT | 86.9 | 0.5 |
| 2,3-DCT | 2.4 | 0.7 |

From the results shown in Table 10, it is seen that when mordenite of the acid type is used as a catalyst, all the isomers of DCT can be formed.

Based on the data showing the adsorption characteristics obtained in Examples 2, 3, 4 and 6 through 10, adsorptive separation of the respective dichlorotoluene isomers was carried out by using a simulated moving bed. The respective dichlorotoluene isomers could be separated at a high efficiency and a high purity.

EXAMPLE 11

2,6-DCT and 2,4-DCT were prepared from a nuclear chlorination product of o-chlorotoluene by the combination of the adsorption step and isomerization step according to the flow shown in FIG. 2.

The same adsorbent, desorbent and simulated moving bed as described in Example 1-(A) were used at the step 37 of adsorptive separation of 2,6-DCT. The same adsorbent and desorbent as described in Example 1-(A) were used at the step 31 of adsorptive separation of 2,4-DCT. The adsorption chamber capacity was changed to 24 ml. At both the steps, the adsorption temperature was adjusted to 150° C. The same catalyst as used in Example 5 was used at the isomerization step 32. The isomerization reaction was carried out at a reaction temperature of 290° C. and a WHSV value of 0.2 hr$^{-1}$ based on DCT in the liquid phase in the presence of benzene in an amount of 50% by weight based on DCT. When the compositions of the liquids flowing at the respective steps became constant, the liquids in the respective lines were analyzed by gas chromatography. The obtained results are shown in Table 11.

Incidentally, reference numeral 35' shown in Table 11 is not given in the flow shown in FIG. 2, but reference numeral 35' represents a branch line from the line 35 shown in FIG. 2. The flow of the desorbent at each adsorptive separation step and the flow of benzene used repeatedly at the isomerization step are omitted.

TABLE 11

| Line No. | 38 | 39 | 33 | 34 | 35 | 35' | 36 |
|---|---|---|---|---|---|---|---|
| Flow rate (ml/hr) | 100 | 28.2 | 71.8 | 43.8 | 308.2 | 28.0 | 280.2 |
| Composition (wt. %) 2,6-DCT | 28.7 | 99.7 | 0.8 | | 2.1 | 2.1 | 2.1 |
| 2,4-DCT | 19.4 | | 27.0 | 99.4 | 2.4 | 2.4 | 11.3 |
| 2,3-DCT | 13.3 | 0.2 | 18.5 | | 47.3 | 47.3 | 47.3 |
| 2,5-DCT | 38.4 | 0.1 | 53.4 | 0.2 | 42.4 | 42.4 | 33.0 |
| 3,4-DCT | 0.1 | | 0.1 | | 4.7 | 4.7 | 5.1 |
| Others | 0.1 | | 0.1 | 0.4 | 1.1 | 1.1 | 1.2 |

EXAMPLE 12

By using adsorbents prepared according to the method described in Example 3 or 4, the adsorption selectivities among DCT isomers were measured in the presence of a substituted benzene compound. The DCT isomer mixture used and experimental conditions adopted were the same as those described in Example 3. The concentration of the substituted benzene compound was 50% by weight. The obtained results are shown in Table 12.

In Table 12, the adsorption selectivity is expressed by the $\alpha_{3,5/X}$ value (X indicates DCT other than 3,5-DCT). From the results shown in Table 12, it is seen that in the presence of 1,2,4-trimethylbenzene or 2-chloro-p-xylene, all of the $\alpha_{3,5/X}$ values are larger than 1.0 and 3,5-DCT has a strongest adsorbability among DCT isomers. That is, 3,5-DCT can be separated as the extract component. On the other hand, as shown in Tables 4 and 5, in the absence of a substituted benzene compound, the adsorbability of 3,5-DCT is weakest (the selective adsorbability is expressed by $\alpha_{X/3,5}$).

TABLE 12

| Adsorbent | Substituted Benzene Compound | $\alpha_{3,5-/2,3-}$ | $\alpha_{3,5-/2,4-}$ | $\alpha_{3,5-/2,5-}$ | $\alpha_{3,5-/2,6-}$ | $\alpha_{3,5-/3,4-}$ |
|---|---|---|---|---|---|---|
| Na—Y | 1,2,4-Trimethylbenzene | 4.0 | 2.9 | 1.4 | 1.3 | 1.8 |
| 0.3 Ba—Na—Y | " | 2.9 | 3.6 | 2.8 | 2.5 | 2.1 |
| 0.3 H—Na—Y | " | 1.8 | 2.0 | 1.4 | 1.4 | 1.5 |
| 0.3 Mg—Na—Y | " | 3.0 | 2.1 | 1.5 | 1.4 | 1.7 |
| 0.3 Sr—Na—Y | " | 4.2 | 2.4 | 1.5 | 1.5 | 1.5 |
| 0.3 Ba—Na—X | " | 1.7 | 2.9 | 2.0 | 1.5 | 2.3 |
| 0.3 Ba—Na—Y | 2-Chloro-p-xylene | 2.0 | 4.0 | 2.0 | 2.1 | 1.9 |

EXAMPLE 13

The adsorption selectivities among chloroxylene isomers were measured either in the absence of a substituted benzene compound or in the presence of a substituted benzene compound. In the chloroxylene isomer mixture used, the 2,5-isomer/2,6-isomer/3,4-isomer/2,4-isomer weight ratio was 2/2/1/5. The experimental conditions were the same as those described in Example 3. The concentration of the substituted benzene compond was 50% by weight. The obtained results are shown in Table 13.

From the results shown in Table 13, it is seen that in the system free of a substituted benzene compound, 2,6-chloroxylene cannot be separated but in the presence of a substituted benzene compound such as toluene or chlorobenzene, 2,6-chloroxylene can be separated as the extract component.

TABLE 13

| Adsorbent | Substituted Benzene Compound | $\alpha_{2,6-/2,4-}$ | $\alpha_{2,6-/2,5-}$ | $\alpha_{2,6-/3,4-}$ |
|---|---|---|---|---|
| Na—X | Not used | 1.5 | 1.2 | 0.5 |
| | Toluene | 2.6 | 1.9 | 1.1 |
| | Chlorobenzene | 1.8 | 1.5 | 1.2 |
| 0.2Ag—Na—X | Not used | 2.6 | 1.4 | 0.8 |
| | Toluene | 3.0 | 2.4 | 1.9 |
| 0.1Ag—Na—X | Chlorobenzene | 2.3 | 1.6 | 1.4 |
| 0.3Ag—K—Y | Not used | 1.7 | 0.9 | 1.4 |
| | Toluene | 8.6 | 2.5 | 2.6 |
| Na—Y | Not used | 1.3 | 1.1 | 3.9 |

TABLE 13-continued

| Adsorbent | Substituted Benzene Compound | $\alpha_{2,6\text{-}/2,4\text{-}}$ | $\alpha_{2,6\text{-}/2,5\text{-}}$ | $\alpha_{2,6\text{-}/3,4\text{-}}$ |
|---|---|---|---|---|
| | Toluene | 3.6 | 22.2 | 1.6 |
| | Chlorobenzene | 1.6 | 1.6 | 2.6 |
| 0.3Ca—Na—X | Not used | 1.3 | 1.3 | 0.6 |
| | Toluene | 2.4 | 2.4 | 1.6 |
| 0.3Ba—Na—X | Not used | 1.3 | 0.8 | 0.5 |
| | Toluene | 1.8 | 1.4 | 1.3 |

We claim:

1. A process for continuously separating 2,6-dichlorotoluene in the liquid phase from a liquid dichlorotoluene isomer mixture containing at least 2,6-dichlorotoluene and 2,3-dichlorotoluene by adsorptive separation, in the liquid phase using a simulated moving bed, wherein a zeolite of the x type which contains as cation 100 to 50 mole % of sodium and 0 to 50 mole % of at least one metal selected from the group consisting of silver and cesium is contacted as the adsorbent and 2,6-dichlorotoluene is separated as the liquid extract component in the presence of another substituted benzene compound.

2. A process according to claim 1, wherein the substituted benzene compound is a compound represented by the following general formula (I):

wherein
$R^1$ stands for H or $CH_3$, $R_2$ stands for H, $CH_3$ or Cl and $R^3$ stands for $CH_3$ or Cl, with the proviso that the case where $R^1$ is $CH_3$, $R^2$ is Cl and $R^3$ is Cl is excluded.

3. A process according to claim 1, wherein the substituted benzene compound is at least one member selected from the group consisting of toluene, xylene, chlorotoluene and trimethylbenzene.

4. A process according to claim 1, wherein the substituted benzene compound is at least one member selected from o-xylene, m-xylene, p-xylene, o-chlorotoluene and p-chlorotoluene.

5. A process according to claim 1, wherein the dichlorotoluene isomer mixture is a mixture containing 2,6-dichlorotoluene, 2,3-dichlorotoluene and 2,5-dichlorotoluene.

6. A process according to claim 1, wherein the adsorptive separation is carried out at a temperature of 50° to 250° C. in the liquid phase.

7. A process according to claim 1, wherein the dichlorotoluene isomer mixture is a mixture containing 2,6-dichlorotoluene, 2,3-dichlorotoluene and 2,4-dichlorotoluene and free of 3,5-dichlorotoluene.

8. A process according to claim 1, wherein the dichlorotoluene isomer mixture is a mixture containing 2,6-dicorotoluene, 2,3-dichlorotoluene and 3,5-dichlorotoluene.

9. A process according to claim 1, wherein the dichlorotoluene isomer mixture is a mixture containing 2,6-dichlorotoluene, 2,3-dichlorotoluene and 3,4-dichlorotoluene.

10. A process for continuously separating 2,6-dichlorotoluene and 2,4-dichlorotoluene from a liquid dichlorotoluene isomer mixture containing 2,6-dichlorotoluene, 2,4-dichlorotoluene and 2,3-dichlorotoluene and free of 3,5-dichlorotoluene by adsorptive separation using a simulated bed, in the liquid phase wherein the adsorptive separation is carried out in the presence of another substituted benzene compound by using a zeolite of the x type which contains as cation 100 to 50 mole % of sodium and 0 to 50 mole % of at least one selected from the group consisting of silver and cesium as the adsorbent and the step (a) of separating 2,6-dichlorotoluene as the extract component is combined with the step (b) of separating 2,4-dichlorotoluene as the raffinate component.

11. A process for continuously separating 2,6-dichlorotoluene and 3,5-dichlorotoluene from a dichlorotoluene isomer mixture containing 2,6-dichlorotoluene, 3,5-dichlorotoluene and 2,3-dichlorotoluene by adsorptive separation using a simulated moving bed, wherein the step (a) of separating 2,6-dichlorotoluene as the extract component in the presence of another substituted benzene compound by using a zeolite as the adsorbent is combined with the step (b) of separating 3,5-dichlortoluene as the raffinate component.

12. A process according to claim 11, wherein the absorptive separation is carried out in the liquid phase.

13. A process according to claim 11, wherein the zeolite is a zeolite of the x type which contains as the cation 100 to 50 mole % of sodium and 0 to 50 mole % of at least one metal selected from the group consisting of silver and cesium.

14. A process for continuously separating 2,6-dichlorotoluene from a dichlorotoluene mixture containing 2,6-dichlorotoluene and 2,3-dichlorotoluene by adsorptive separation using a simulated moving bed, in the liquid phase, wherein the step (a) of continuously separating 2,6-dichlorotoluene as the extract component in the presence of another substituted benzene compound by using a faujasite type zeolite of the x type which contains as cation 100 to 50 mole % of sodium and 0 to 50 mole % of at least one metal selected from the group consisting of silver and cesium as the adsorbent in the liquid phase, is combined with the step (b) of isomerizing the raffinate component formed at the step (a), and the reaction liquid from the isomerizing step (b) is recycled to the adsorptive separation step (a).

15. A process for continuously separating 2,6-dichlorotoluene and separating or preparing one or two dichlorotoluene isomers presented by the following formula (II):

wherein
one of X, Y, and Z stands for $CH_3$ and the remaining members stand for Cl, from a dichlorotoluene isomer mixture containing 2,6-dichlorotoluene, 2,3-dichlorotoluene and at least one dichlorotoluene isomer of the above formula (II), which comprises, in combination:

the step (a) of continuously separating 2,6-dichlorotoluene as the extract component in the presence of another substituted benzene compound by using a faujasite type zeolite as the adsorbent in a simulated moving bed;

the step (b) of isomerizing a dichlorotoluene isomers, other than the dichlorotoluene isomer of the above formula (II) to be separated or prepared, or isomerizing a dichlorotoluene isomer mixture containing said dichlorotoluene isomer to be separated or prepared, by using a catalyst composed of a crystalline aluminosilicate zeolite of the acid type having an X-ray diffraction pattern having peaks at positions of lattice spacings d of 11.2±0.2 Å, 10.1±0.2 Å, 3.86±0.08 Å, 3.72±0.08 Å, and 3.66±0.08 Å, thereby to prepare said dichlorotoluene isomer to be prepared or to increase the content of said dichlorotoluene isomer to be prepared, and, the step (c) of separating said dichlorotoluene isomer to be separated or prepared.

16. A process according to claim 15, wherein said dichlorotoluene isomer mixture contains at least 2,6-dichlorotoluene and 2,4-dichorotoluene and is supplied to the step (a) of adsorptive separation of 2,6-dichlorotoluene; the remaining dichlorotoluene isomer mixture is supplied to the separation step (c) where 2,4-dichlorotoluene is adsorptively separted continuously by using a simulated moving bed; the remaining dichlorotoluene isomer is supplied to the isomerization step (b) where the concentration of 2,4-dichlorotoluene is increased; and the isomerized dichlorotoluene mixture is recycled to the separation step (c).

17. A process according to claim 15, wherein said dichlorotoluene isomer mixture containing 2,6-dichlorotoluene and at least one dichlorotoluene isomer of the formula (II) is supplied to the step (a) of adsorptive separation of 2,6-dichlorotoluene; the remaining dicholorotoluene isomer mixture is supplied to the isomerization step (b) where 3,4-dichlorotoluene is prepared by isomerization; the isomerized dichlorotoluene mixture is supplied to the separation step (c) where 3,4-dichlorotoluene is separated by distillation; and the remaining dichlorotoluene isomer mixture is recycled to the isomerization step (b).

18. A process according to claim 15, wherein the catalyst is at least one zeolite selected from zeolite ZSM-5, zeolite zeta-3 and a crystalline aluminosilicate zeolite formed by reacting an aqueous reaction mixture containing a silica source, an alumina source, an alkali source and a carboxyl group-containing organic compound.

19. A process according to claim 15, wherein a zeolite in which the SiO$_2$/Al$_2$O$_3$ molar ratio is in the range of from 15 to 100 is used as the catalyst.

20. A process according to claim 15, wherein the isomerization reaction is carried out in the liquid phase.

21. A process according to claim 15, wherein the isomerization reaction is carried out in the presence of at least one compound selected from the group consisting of benzene and chlorobenzene.

22. A process according to claim 15, wherein the separation of 2,6-dichlorotoluene is carried out in the liquid phase.

23. A process according to claim 15, wherein the zeolite is a zeolite of the x type which contains as the cation 100 to 50 mole % of sodium and 0 to 50 mole % of at least one metal selected form the group consisting of silver and cesium.

24. A process for continuously separating 3,5-dichlorotoluene from a dichlorotoluene isomer mixture by adsorptive separation using a simualted moving bed, wherein a faujasite type zeolite adsorbent is used as the adsorbent and 3,5-dichlorotoluene is separated as the extract component in the presence of at least one compound selected from the group consisting of 1,2,4,-trimethylbenzene and 2-chloro-p-xylene.

25. A process according to claim 24, wherein the faujasite type zeolite contains at least a sodium cation.

26. A process according to claim 24, wherein the faujasite type zeolite contains at least sodium and barium cations.

27. A process for continuously separating 2-chloro-m-xylene from a chloroxylene isomer mixture by adsoprtive separation using a simulated moving bed, wherein a faujasite type zeolite is used as the adsorent and 2-chloro-m-xylene is separated as the extract compoent in the presence of a substituted benzene compound.

28. A process according to claim 27, wherein the substituted benzene compound is at least one member selected from the group consisting of toluene and chlorobenzene.

29. A process according to claim 27, wherein the faujasite type zeolite contains at least one cation selected from the group consisting of sodium, potassium, barium, calcium and silver.

30. In a method of separating 2,6-dichlorotoluene from a liquid mixture also containing at least its 2,3-isomer, the steps which comprise:

a. establishing a simulated moving adsorbent bed which includes an x-type zeolite containing as cation 100–50 mole sodium and 0–50 mole % of at least one metal selected from the group consisting of silver and cesium, b. including in said liquid mixture a substituted benzene compound of the formula (I)

wherein R$^1$ stands for H or CH$_3$, R$^2$ stands for H, CH$_3$ or Cl and R$^3$ stands for CH$_3$ or Cl, with the proviso that the case where R$^1$ is CH$_3$, R$^2$ is Cl and R$^3$ is Cl is excluded, c. contacting said mixture in the liquid phase with said adsorbent bed, d. selectively adsorbing 2,6-dichlorotoluene on said adsorbent in the presence of said substituted benzene compound, and e. recovering said 2,6-dichlorotoluene from said adsorbent.